United States Patent [19]
Riley et al.

[11] Patent Number: 5,857,250
[45] Date of Patent: Jan. 12, 1999

[54] METHOD OF FORMING A CAPACITANCE TYPE GASEOUS SENSING DEVICE AND APPARATUS THEREOF

[75] Inventors: Scott J. Riley, McKinney; Kenneth J. Balkus, Jr., The Colony; Bruce E. Gnade, Dallas, all of Tex.

[73] Assignee: Texas Instruments Incorporated, Dallas, Tex.

[21] Appl. No.: 329,003

[22] Filed: Oct. 25, 1994

[51] Int. Cl.[6] ..................................................... H01G 7/00
[52] U.S. Cl. .......................................... 29/25.42; 361/280
[58] Field of Search .................................... 361/277, 278, 361/280–282, 286, 303, 305, 311; 422/88–90, 98; 324/663; 1117/50; 438/60, 919; 29/25.03, 25.02, 25.01, 25.41, 25.42; 73/31.01, 31.02, 31.05, 31.06, 31.03; 338/34; 204/421, 424–426, 431; 502/564–70

[56] References Cited

U.S. PATENT DOCUMENTS

| | | | |
|---|---|---|---|
| 4,860,584 | 8/1989 | Mercer et al. | 73/336.5 |
| 5,124,021 | 6/1992 | Kaneyasu et al. | 204/426 |
| 5,143,696 | 9/1992 | Haas et al. | 422/90 |
| 5,372,785 | 12/1994 | Johnson et al. | 422/90 |
| 5,386,798 | 2/1995 | Lowndes et al. | 117/50 |

*Primary Examiner*—Leo P. Picard
*Assistant Examiner*—Phuong T. Vu
*Attorney, Agent, or Firm*—Mark A. Valetti; Jacqueline J. Garner; Richard L. Donaldson

[57] ABSTRACT

The capacitance type gaseous sensing device (10) includes a first electrode layer (12) formed on a semiconductor substrate layer (14). A seed layer (16) is formed on the first electrode layer (12). A reorganized layer (18) is formed on the first electrode layer (12) through interaction with the seed layer (16) to form a porous sensing layer. A second electrode layer (20) is formed on the reorganized layer (18). The reorganized layer (18) absorbs gaseous elements that change the dielectric constant of the capacitance type sensor device (10). A change in the dielectric constant causes a change in the capacitance of the reorganized layer (18) as measured across the first electrode layer (12) and the second electrode layer (20).

11 Claims, 2 Drawing Sheets

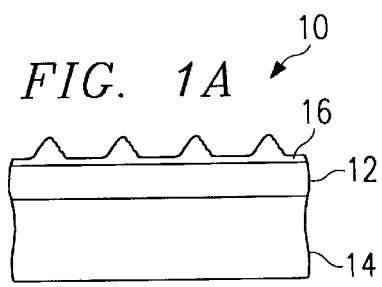
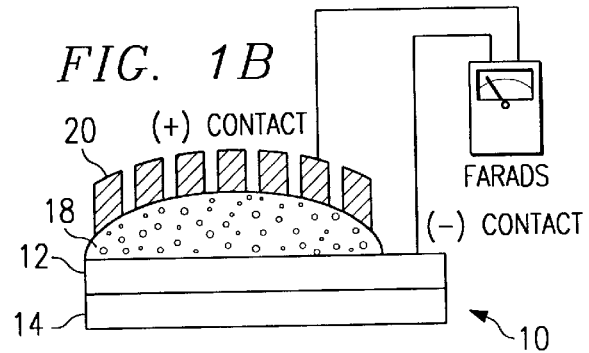
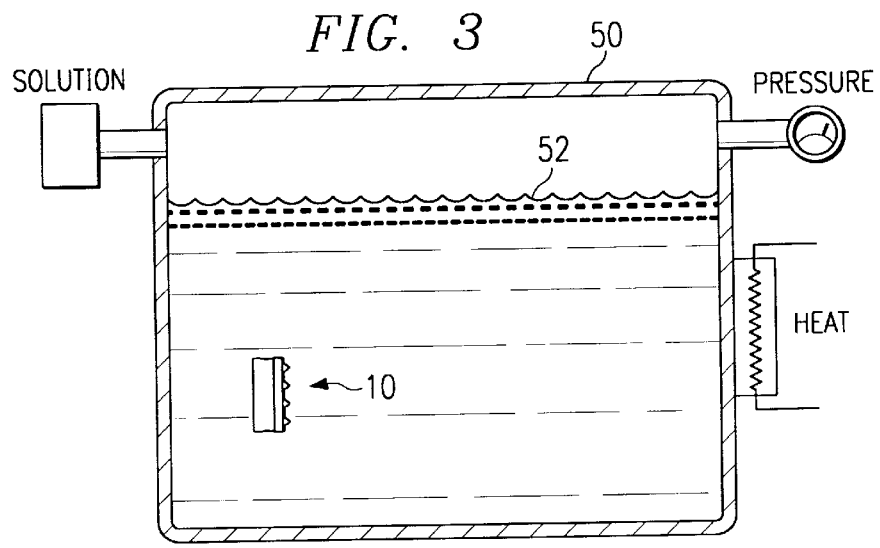
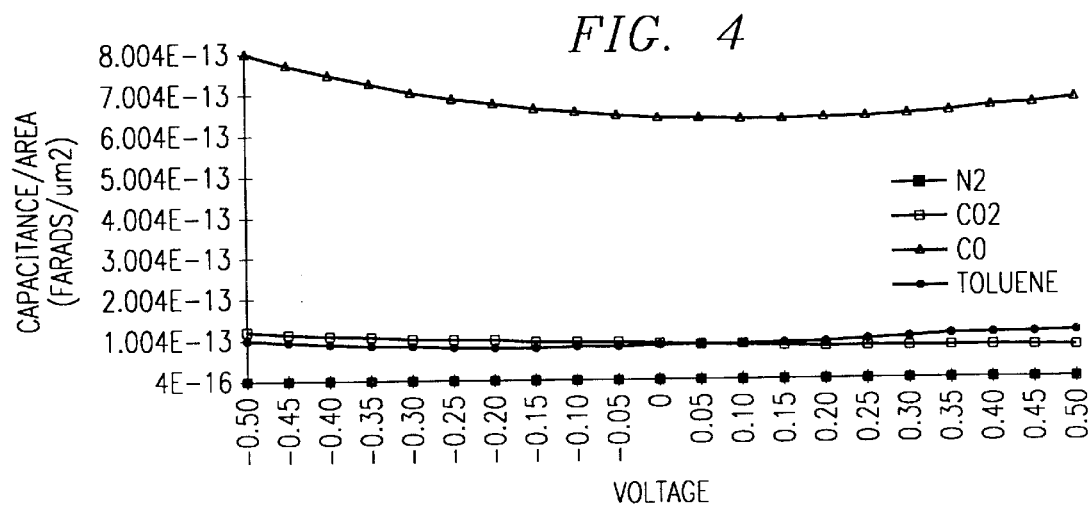

METHOD OF FORMING A CAPACITANCE TYPE GASEOUS SENSING DEVICE AND APPARATUS THEREOF

TECHNICAL FIELD OF THE INVENTION

The present invention relates in general to devices for sensing gaseous emissions and more particularly to a method of forming a capacitance type gaseous sensing device and apparatus thereof.

BACKGROUND OF THE INVENTION

Increasing concern over the daily emission of both toxic and greenhouse gases has prompted the need for more sensitive and selective gas sensors. Legislation restricting the current and future emission of these gases from sources such as internal combustion engines indirectly requires the improvement of sensors to detect gases such as carbon dioxide, carbon monoxide, and nitrous oxide. Modern sensors rely on the interactions between sensor and analyte to produce a detectable change in either the electrical, optical, mechanical, electrochemical, or thermal properties of the sensor. This interaction can take the form of physisorption, chemisorption, or catalysis.

A sensor that relies on physisorption has the advantage of being easily refreshed. However, physisorption involves weak attractive forces which present difficulties in establishing analyte detection. Chemisorption sensors rely on the chemical bonding of the analyte molecules to the probe surface to produce a detectable change in the electrical conductivity mass, capacitance, or optical properties of that surface. Difficulties arise when the sensor is in continual use as it is necessary to expose a fresh probe surface to the incoming analyte due to the chemical bonding of the analyte molecules. Catalytic sensors transform the analyte to a different compound, yielding a detectable change of heat. A major disadvantage of catalytic sensors lie in their inability to detect compounds that are chemically stable.

Low density molecular sieves have been shown to be useful as selective chemical sensors. Zeolites are one of the several groups that comprise the structural family of microporous metal oxides known as molecular sieves. Zeolites are crystalline aluminum silicates that have three dimensional networks of connected channels or cages. A molecular sieve based sensor might be used to selectively detect those molecules which can readily absorb into the zeolite cages.

Zeolite molecular sieves have been employed as the active component in surface acoustic wave devices and piezo electric quartz crystal microgravometric type sensors. These approaches involve either a thin film configuration as a ceramic composite or the zeolites are tethered to an electrode surface via organic linkages. The sensing ability of these devices depends on changes in either mass or electrical properties produced by the absorption of the analyte. The sensing characteristics are limited in that a detectable mass change is required and the circuitry needed to detect a change in mass is relatively complicated. Further, these approaches cannot discriminate between analyte molecules of similar size and shape. Another problem is that it is very difficult to deposit uniform thin films of low density molecular sieve material in order to fabricate a reliable gaseous sensor. Therefore, it is desirable to have a gaseous sensor that has a uniform film layer and can discriminate between different types of absorbed analytes.

SUMMARY OF THE INVENTION

From the foregoing it may be appreciated that a need has arisen for a gaseous sensor with a thin uniform film of a low density molecular sieve material. A need has also arisen for a capacitance type sensor that can discriminate between different absorbed analytes.

In accordance with the present invention, there is provided a method of forming a capacitance type gaseous sensing device and apparatus thereof are provided which substantially eliminate and reduce disadvantages and problems associated with other physisorption, chemisorption, or catalysis type sensors.

According to an embodiment of the present invention, there is provided a method of forming a capacitance type gaseous sensing device that includes forming a first electrode layer onto a semiconductor substrate layer. A reorganized layer of a molecular sieve material is uniformly formed onto the electrode layer while maintaining surface crystallinity of the reorganized layer. A second electrode layer is formed on selected portions of the reorganized layer in order to establish the capacitance type sensor. The uniformity of the reorganized layer may be achieved through a prior formation of a seed layer on the first electrode layer.

The present invention provides various technical advantages over physisorption, chemisorption, or catalysis type sensors. For example, one technical advantage is in having a reliable capacitance type sensor device. Another technical advantage is in having a gaseous sensor with a uniform layer of a molecular sieve material. Yet another technical advantage is in using a seed layer to establish uniformity of the reorganized layer and provide a very thin layer for increased capacitance while allowing for selective absorption. Other technical advantages are readily apparent to one skilled in the art from the following figures, description, and claims.

BRIEF DESCRIPTION OF THE DRAWINGS

For a more complete understanding of the present invention and the advantages thereof, reference is now made to the following description taken in conjunction with the accompanying drawings, wherein like reference numerals represent like parts, in which:

FIGS. 1A–B illustrate cross-sectional drawings depicting the process steps in forming a capacitance type gaseous sensing device;

FIG. 3 illustrates a hydrothermal process used in fabricating the capacitance type gaseous sensing device; and FIG. 4 illustrates a plot depicting capacitance levels for different gaseous elements absorbed by the capacitance type gaseous sensing device.

DETAILED DESCRIPTION OF THE INVENTION

Figure 2:
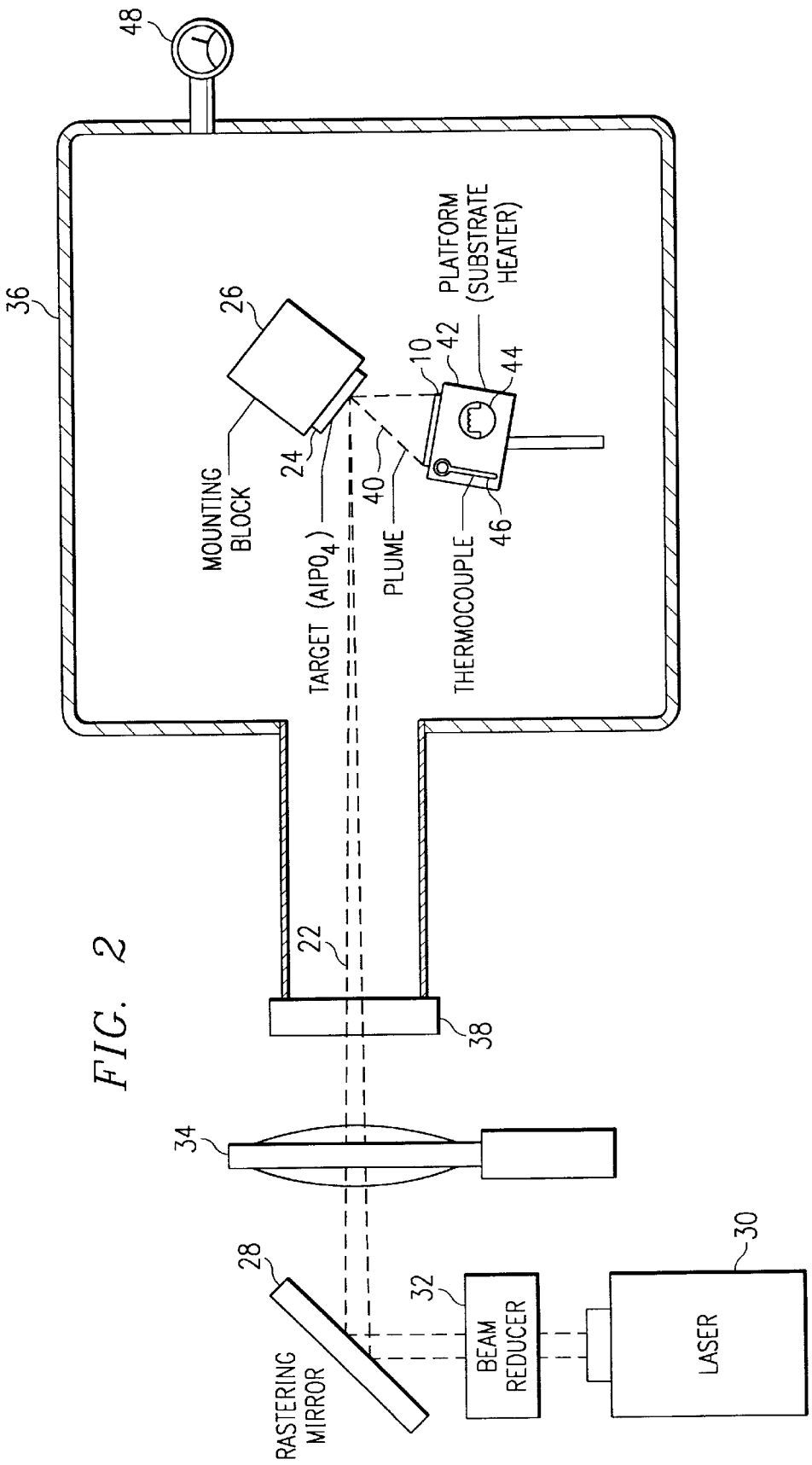
FIG. 2 illustrates a pulse laser ablation process used during fabrication of the capacitance type gaseous sensing device.

FIGS. 1A–B show the process steps in forming a capacitance type gaseous sensing device 10. Capacitance type gaseous sensing device 10 is made by forming a first electrode layer 12 onto a semiconductor substrate 14. A seed layer 16 is formed over portions of first electrode layer 12. Referring to FIG. 1B, a reorganized layer 18 is formed on seed layer 16 and first electrode layer 12 to establish a pore sensing layer for capacitance type gaseous sensing device 10. A second electrode layer 20 is formed onto selected portions of reorganized layer 18.

In operation, capacitance type gaseous sensing device 10 absorbs gaseous emissions into the porous sensing layer formed by reorganized layer 18 and seed layer 16. The absorption of gases within the porous sensing layer causes a change in the dielectric constant of the porous sensing layer. This change in the dielectric constant is measured as a change in capacitance across first electrode layer 12 and second electrode layer 20. Different gases absorbed by the porous sensing layer cause different changes in capacitance for capacitance type gaseous sensing device 10. Only certain gases can be absorbed by certain molecular sieve materials, therefore the material used in the porous sensing layer can be selected for specific gaseous detection.

In order to register large capacitance values, the porous sensing layer of capacitance type gaseous sensing device 10 is of a thin dielectric film in order to maintain a small distance between first electrode layer 12 and second electrode layer 20. Further, the very thin films of a neutral lattice molecular sieve form the material for the porous sensing layer in order to achieve a sensitive and selective capacitance type chemical sensor. Molecular sieve materials that provide good sensing characteristics and used in forming the porous sensing layer include aluminum phosphates and metal aluminum phosphates. An aluminum phosphate based molecular sieve material works well due to its insulating properties.

First electrode layer 12 and second electrode layer 20 preferably are made of oxidation resistant or inert metal materials that stand up to the formation of the porous sensing layer. Materials that satisfy the characteristics for first electrode layer 12 and second electrode layer 20 include titanium nitride, gold, palladium, and platinum.

FIG. 2 shows a simplified block diagram depicting how seed layer 16 is formed onto first electrode layer 12. Seed layer 16 may be formed onto first electrode layer 12 by a pulse laser ablation process. The pulse laser ablation process may occur by directing a laser beam 22 onto a target 24 made of the molecular sieve material. Target 24 is placed on a mounting block 26 and laser beam 22 is directed across target 24 by a rastering mirror 28. Rastering mirror 28 receives laser beam 22 from an excimer laser 30 through a beam reducer 32. Rastering mirror 28 allows laser beam 22 to be moved across target 24 instead of ablating material from a single spot of target 24. Laser beam 22 is further reduced by a lens 34 before entering a vacuum chamber 36 through a quartz window 38. A plume of material 40 is emitted from target 24 as a result of ablation caused by laser beam 22. Plume 40 comes in contact with first electrode layer 12, causing seed layer 16 to form thereon. Seed layer 16 is formed of molecular sieve fragments that form on portions of first electrode layer 12. Semiconductor substrate 14, with first electrode layer 12, is mounted on a platform 42 that includes a lamp 44 and a thermocouple 46 used to heat and set the temperature of capacitance type gaseous sensing device 10 during the ablation process. Vacuum chamber 36 may be controlled through a gas manifold, the chamber pressure ambient being monitored with a pressure gauge 48.

FIG. 3 shows a hydrothermal process used in placing reorganized layer 18 onto seed layer 16 and first electrode layer 12. After pulse laser ablation, semiconductor substrate 14 is placed into a chamber 50 having an aqueous solution 52 that includes the precursor chemicals required to make the molecular sieve material. Chamber 50 may be pressurized through pressure regulator 54 and heated by heating element 56 to allow for hydrothermal growth of gel mixture 52 onto seed layer 16 and first electrode layer 12 of capacitance type gaseous sensing device 10. Capacitance type gaseous sensing device 10 is preferably placed such that seed layer 16 faces down to allow for pure growth of reorganized layer 18 without any accumulations due to gravity. The hydrothermal process causes seed layer 16 to reorganize with the growth of reorganized layer 18. Reorganized layer 18 may have the same thickness as seed layer 16. During the process, the morphology changes from amorphous looking spheres to faceted particles. The ablated surface of the first electrode layer 12 composed largely of molecular sieve fragments reorganize and seed the gel mixture 52 in order to create the porous sensor layer. The hydrothermal treatment of the ablated surface leads to enhanced surface crystallinity of the porous sensing layer.

The fabrication of a capacitance type gaseous sensing device 10 will now be discussed with reference to a specific embodiment. A titanium nitride first electrode layer 12 is formed on semiconductor substrate 14. Semiconductor substrate 14 and titanium nitride first electrode layer 12 are placed on platform 42 of the pulse laser ablation process. Target 24 consisting of aluminum phosphate $AlPO_4$-5 was prepared by pressing approximately one gram of the molecular sieve material into a one inch die. Target 24 is placed on mounting block 26. Excimer laser 30 using krypton fluoride radiation generates a 248 nanometer wavelength laser beam 22 with a power density of $10^6 W/CM^2$. Laser pulse energies from 50 mJ to 400 mJ with pulse repetition rates from 1 to 80 pulses per second may be employed. Laser beam 22 is reduced to a diameter of 1.7 centimeters by beam reducer 32 before being reflected off of rastering mirror 28. Rastering mirror 28 is used to position laser beam 22 along any portion of target 24. Laser beam 22 is further reduced by a 10 inch focal length convex lens 34 to a 1 millimeter size spot on target 24. Laser beam 22 enters vacuum chamber 36 through quartz window 38 and contacts target 24 mounted at an angle of 35° relative to laser beam 22. Lamp 44 is turned on to heat semiconductor substrate layer 14 and titanium nitride first electrode layer 12 to temperatures in the range of 150° C. to 350° C. Vacuum chamber 36 is pressurized through gas manifold and pressure gauge 48 to pressures in the range of 0.15 to 0.45 Torr using either oxygen, template such as tripropylamine or dicyclohexylamine, and oxygen, water and oxygen, or water vapor. Ablation of target 24 aluminum phosphate molecular sieve material generated a visible plume of material that varies in size, shape, and color depending upon the experimental conditions. The molecular sieve material of plume 40 deposits onto titanium nitride first electrode layer 12 as molecular sieve fragments.

In order to enhance the crystallinity of seed layer 16, capacitance type gaseous sensing device 10 is subjected to a post hydrothermal treatment. Capacitance type gaseous sensing device 10 is placed in a teflon lined chamber 50 containing an aluminum phosphate $AlPO_4$ gel mixture designed to prepare aluminum phosphate $AlPO_4$-5. Chamber 50 is heated to a temperature of 150° C. for a process time of 1 to 24 hours. Chamber 50 is also pressurized to approximately 30 Psi. During hydrothermal treatment, the ablated molecular sieve film, seed layer 16, reorganizes under the hydrothermal conditions with the aluminum phosphate gel mixture 52. Seed layer 16 allows for the deposition of partially crystalline aluminum phosphate molecular sieve material of reorganized layer 18 onto titanium nitride first electrode layer 12. Selective vapor deposition of gold/palladium onto portions of reorganized layer 18 create second electrode layer 20.

FIG. 4 shows a plot of capacitance per square micron for a 70.3 nanometer thick aluminum phosphate $AlPO_4$-5 molecular sieve measured from between −0.5 to +0.5 volts and an oscillator frequency of 100 kHz exposed to different gas ambients. As seen in the plot, the nitrogen response is 100 times greater than the instrument noise level of $10^{-16}$ farads. Upon exposure to atmospheres of carbon dioxide or toluene, the capacitance increases nearly 1000 times. The response to carbon monoxide is almost 10 times greater than that of carbon dioxide. This is consistent with a highly polar carbon monoxide molecule strongly absorbing into the molecular sieve material. The plot shows that capacitance type gaseous sensing device 10 can discriminate between different gaseous elements. It is possible to reverse the changes in capacitance of capacitance type gaseous sensing device 10 for later reuse through temperature or pressure adjustments.

Uniform thin films of low density molecular sieves can be produced on semiconductor compatible materials, using semiconductor compatible processes. Such a technique allows for the capability to build integrated circuits within semiconductor substrate layer 14 for use in controlling and evaluating capacitance type gaseous sensing device 10. An integrated circuit may be fabricated within semiconductor substrate layer 14 to produce a detection signal when a gaseous element is absorbed into reorganized layer 18. When the integrated circuit process is complete, the molecular sieve material can be deposited on first electrode layer 12. The molecular sieve material can be deposited at the wafer level in order to reduce processing costs. Once the molecular sieve material is deposited, second contact layer 20 is deposited and bonded to the integrated circuit. The entire molecular sieve material deposition could be performed as a back end process so that the molecular sieve material would not enter a wafer fabrication. This process flow provides a completely monolithic silicon based chemical sensor.

In summary, a capacitance type gaseous sensing device is fabricated by forming a uniform reorganized layer between two electrode layers. The uniform reorganized layer is formed by forming a seed layer on a first electrode layer through pulse laser ablation of molecular sieve material. Hydrothermal treatment is performed on the device in order to grow a reorganized layer onto the first electrode layer through interaction with the seed layer. A second electrode layer is formed onto the reorganized layer in order to establish the capacitance type gaseous sensing device. In operation, the reorganized layer absorbs gaseous elements which change the dielectric constant of the device. A change in dielectric constant causes a change in capacitance in the reorganized layer which is measured across the first and second electrode layers.

Thus, it is apparent that there has been provided, in accordance with the present invention, a method of forming a capacitance type gaseous sensing device and apparatus thereof that satisfy the advantages set forth above. Although the preferred embodiment has been described in detail, it should be understood that various changes, substitutions, and alterations can be made herein. For example, though specific materials and process parameters have been described, other materials and process parameters may be used and varied in order to achieve reliable sensing properties. Other examples are readily ascertainable by one skilled in the art and could be made without departing from the spirit and scope of the present invention as defined by the following claims.

What is claimed is:

1. A method of forming a capacitance type sensor, comprising the steps of:

forming a first electrode layer onto a semiconductor substrate layer, said first electrode is comprised of titanium nitrate;

forming a seed layer onto a portion of said first electrode layer, said seed layer comprising an aluminum phosphate molecular sieve material;

uniformly forming a reorganized layer that incorporates said seed layer onto the first electrode layer, the reorganized layer having a surface crystallinity, the reorganized layer being form of the aluminum phosphate molecular sieve material; and forming a second electrode layer onto selected portions of the reorganized layer, said second electrode is comprised of gold palladium.

2. The method of claim 1, wherein said seed layer forming step is performed by pulsed laser ablation of the molecular sieve material.

3. A method of forming a capacitance type sensor, comprising the steps of:

forming a first electrode layer onto a semiconductor substrate layer;

forming a seed layer onto a portion of said first electrode layer, said seed layer comprising an aluminum phosphate molecular sieve material;

uniformly forming a reorganized layer that incorporates said seed layer onto the first electrode layer, the reorganized layer having a surface crystallinity, the reorganized layer being form of the aluminum phosphate molecular sieve material;

forming a second electrode layer onto selected portions of the reorganized layer and wherein said uniformly forming step is performed by hydrothermal treatment of the molecular sieve material.

4. The method of claim 1, wherein the molecular sieve material is selected to detect carbon monoxide.

5. The method of claim 1, further comprising the step of:

forming an electric circuit within the semiconductor substrate layer, the electric circuit operable to detect a change in capacitance of the reorganized layer across the first and second electrode layers.

6. The method of claim 1, further comprising the steps of:

heating the first electrode layer and the semiconductor substrate layer;

pressurizing the first electrode layer and the semiconductor substrate layer.

7. A method of forming a capacitance type sensor, comprising the steps of:

depositing a first electrode layer onto a semiconductor substrate layer, the first electrode layer being formed of an oxidation resistant or inert metal;

depositing a seed layer onto a portion of the first electrode layer by pulsed laser ablation of a target, the target and the seed layer being formed of a low density molecular sieve material;

hydrothermally treating the seed layer to establish a reorganized layer on the first electrode layer, the reorganized layer being formed of the molecular sieve material, the reorganized layer being uniformly grown onto the first electrode layer with a crystalline surface in response to reactions with the seed layer;

depositing a second electrode layer onto a portion of the reorganized layer, the second electrode layer being formed of an oxidative resistant or inert metal.

8. The method of claim 7, wherein the pulsed laser ablation is performed using a rasterizing mirror to move a laser beam across the target to avoid ablating the target at one spot.

9. The method of claim 8, further comprising the step of:

adjusting a pulse rate for the pulsed laser ablation in order to vary a thickness and crystallinity of the seed layer.

10. The method of claim 7, further comprising the step of:

heating the semiconductor substrate layer and the first electrode layer.

11. The method of claim 7, further comprising the step of:

pressurizing the semiconductor substrate layer and the first electrode layer.

* * * * *